(12) United States Patent
Rebier

(10) Patent No.: US 6,322,818 B1
(45) Date of Patent: Nov. 27, 2001

(54) STARCH GRANULATION

(75) Inventor: Jean-Michel Rebier, Calais (FR)

(73) Assignee: Cerestar Holding B.V., Sas van Gent (NL)

( * ) Notice: Subject to any disclaimer, the term of this patent is extended or adjusted under 35 U.S.C. 154(b) by 0 days.

(21) Appl. No.: 09/624,394

(22) Filed: Jul. 24, 2000

(30) Foreign Application Priority Data

Jul. 24, 1999 (GB) .................................... 9917339

(51) Int. Cl.⁷ ................................ A61K 9/14; A61K 9/50
(52) U.S. Cl. ............................................ 424/489; 424/499
(58) Field of Search ...................................... 424/489, 499

(56) References Cited

U.S. PATENT DOCUMENTS 5,888,548 * 3/1999 Wongsuragrai et al. ............ 424/489

FOREIGN PATENT DOCUMENTS

357144952A * 9/1982 (JP) .

WO 95/19376    7/1995 (WO) .

OTHER PUBLICATIONS

Patent Abstracts Of Japan, vol. 006, No. 224 (C–138), Dec. 2, 1982 (Dec. 02, 1982) & JP 57 144952 A (Hokuren Nougiyou Kiyoudou Kumiai Rengoukai), Sep. 7, 1982 (Sep. 07, 1982).

* cited by examiner

Primary Examiner—Thurman K. Page
Assistant Examiner—Rachel M. Bennett
(74) Attorney, Agent, or Firm—Fitch, Even, Tabin & Flannery

(57) ABSTRACT

The present invention relates to starch granules made completely on the basis of starch and to a process for producing these granules. The process comprises the use of a slurry of pregelatinised starch and starch granules to coat in multiple layers starch seeds. The granules so obtained are useful for immobilisation of desired products, which include such divers products as enzymes, pharmaceuticals, colorants, flavours.

16 Claims, No Drawings

STARCH GRANULATION

TECHNICAL FIELD

The present invention relates to agglomerated, substantially spherical starch particles made completely on the basis of starch and to a process for producing these particles. The process comprises the use of completely pregelatinised starch as binder for starch granules. The particles so obtained are useful for immobilisation of desired products, which include such divers products as enzymes, pharmaceuticals, colorants, flavours, carotenoids, vitamins, antifoams.

BACKGROUND OF THE INVENTION

There is a growing interest in the addition of specific ingredients or additives to food, feed, detergents, cosmetics, chemicals etc. The form wherein these ingredients or additives are added will depend on the physical and chemical characteristics. Some components are so active that they have to be added in diluted forms, others are prone to oxidation or are very hygroscopic so that they have to be packaged in one form or another.

One way of packaging the ingredients or additives is by enclosing them in capsules other possibilities include the enclosure or entrapment in a gel or gellifying agent or the binding to a carrier.

Different types of carrier materials are known, depending on the specific component and on the desired application a carrier is chosen. For some applications or components there are still no suitable carriers available. Starch-based carriers have been investigated for some time. In general when starch is used as a carrier the final, loaded particles are not strong or hard enough. Alternatively they do not degrade fast enough.

British Patent Application GB 2,311,534 A discloses starch particles comprising 30–95% starch and/or low-protein flour; 0.1–50% silicon dioxide; and 5–15% water. As indicated in the summary of the invention, bridging pages 1 and 2 the silicon dioxide is added to improve the flowability of starch granules.

European Patent Application EP 402 186 A discloses a process for preparing directly compressible starch. In this process a part of the starch is heated for some time to around 80° C. This temperature is however not enough to fully pregelatinise the starch.

Japanese patent application JP 56028606 relates to the preparation of granular potato starch. It discloses a process wherein potato starch is charged in a fluidising granulator and a solution of gelatinised potato starch is sprayed as a binder. The fluidised potato starch agglomerates and grows surrounding the binder nucleus to obtain fine granular potato starch.

PCT application WO 95/19376 relates to a porous particle aggregate and methods for the preparation thereof. It relates to substantially spherical porous aggregates of starch granules bound together with a binder at least at their points of contact and said starch granule aggregates having an average diameter of about 5 to about 250 microns. The porous particle aggregate is prepared by spray-drying.

There is a need for a carrier material consisting of substantially spherical particles with an improved hardness and composed of starch exclusively. Such a product can therefore easily be applied in food, feed and pharmaceutical applications.

SUMMARY OF THE INVENTION

The present invention discloses agglomerated, substantially spherical particles characterised in that the particle is comprising 100% starch (w/w) and said particle consists of successive layers comprising starch granules and pregelatinised starch and said particle has a diameter of from 50 $\mu$m to 3 mm, preferably of from 100 $\mu$m to 2 mm, more preferably of from 300 $\mu$m to 800 $\mu$m.

The starch used for making the particles can be any type of starch for example the starch is selected from the group consisting of rice, wheat, corn, potato, sago, bean and tapioca starch and mixtures thereof. It is possible to use mixtures of different types of starch. It is also possible to use chemically or physically modified starches or hydrolysed starch materials.

The present invention also discloses agglomerated particles containing in addition to starch, enzymes, pharmaceuticals, colorants, flavours, carotenoids, and/or vitamins.

A process for producing the agglomerated, substantially spherical starch particles of the present invention is also disclosed and comprises the following steps: Starch seeds are sprayed with a slurry of starch granules and pregelatinesed starch, and the seeds are layered with the slurry, the spraying and subsequent layering is repeated until the particles have reached a final diameter of from 50 $\mu$m to 3 mm.

The present invention further relates to a process wherein enzymes, pharmaceuticals, colorants, flavours, carotenoids, vitamins and/or antifoams are added to the slurry of starch granules and pregelatinised starch, or to the last layer when the particles are reaching the final diameter.

The present invention further relates to a process comprising the following steps:
a) Preparing agglomerated substantially spherical starch particles according to the process aforementioned, and
b) Covering the agglomerated substantially spherical starch particles with enzymes, pharmaceuticals, colorants, flavours, carotenoids, vitamins and/or antifoams.

The process is performed in a fluid bed reactor, fluid drum granulator or a blender.

DETAILED DESCRIPTION OF THE INVENTION

The present invention discloses agglomerated, substantially spherical particles characterised in that the particle is comprising 100% starch (w/w) and said particle consists of successive layers comprising starch granules and pregelatinised starch and said particle has a diameter of from 50 $\mu$m to 3 mm, preferably of from 100 $\mu$m to 2 mm, more preferably of from 300 $\mu$m to 800 $\mu$m.

Such particles are made completely from starch and can be used as such or can act as a carrier, which makes them suitable for a whole series of applications, including addition to food or feed.

It is recognised that the desired diameter of the particles will depend on their intended application. By the processes of the present invention particle wherein successive layers are formed, diameters of up to 3 mm can be reached.

The desired application and the diameter will also have an effect on the preferred type of starch. The starch granules themselves have a certain diameter so that it becomes difficult to make particles of for example less than 100 $\mu$m from potato starch knowing that potato starch granule diameters are in the range of from 10 $\mu$m to 100 $\mu$m. As a rough measure it should be kept in mind that the diameter of some of the useful starch granules are as follows: rice starch 1 $\mu$m to 5 $\mu$m, wheat starch 3 $\mu$m to 50 $\mu$m, corn starch 10 $\mu$m to 30 $\mu$m and potato starch 10 $\mu$m to 100 $\mu$m.

The processes of the present invention are equally applicable to all kinds of starches such as rice, wheat, corn, potato, sago, bean and tapioca starch or mixtures thereof. Although it may be most practical to use the same type of starch providing the starch granules and pregelatinised starch, it is of course possible to combine different types of starches. The pregelatinised starch and the starch granules may therefore be different. It is further possible to use different types of starch granules or use mixed starches for pregelatinisation. In such cases it may be useful to sieve the starch granules to obtain more or less the same granule diameter.

In addition to the native starches it is also possible to perform the granulation process on physically or chemically modified starches or on hydrolysed starch based products (i.e. maltodextrins, dextrose)

The starch particles are essentially onion-type agglomerates wherein starch seeds are layered or coated with a slurry of starch granules and pregelatinised starch. These particles may be obtained by different types of agglomeration or granulation processes, which allow layering or coating for obtaining a substantially spherical particle with a big diameter. The essence of the process for obtaining the agglomerates of the starch granules is that starch seeds are sprayed with a slurry of starch granules and pregelatinised starch and the seeds are layered with the slurry, and the spraying and layering are continued until a final diameter of from 50 µm to 3 mm is reached. It is obvious that in order to obtain a spherical particle the starch seeds have to be in constant, more or less, free motion otherwise lumps are formed. The slurry of starch granules and pregelatinised starch has a dry substance content of at least 20% w/w.

One example of a suitable process for making the agglomerated particles is a fluid bed another is the use of a rotating drum, or a blender of any type.

In one of the modes of applying the process of the present invention starch seeds are brought into a fluid bed and are then sprayed with a slurry of starch granules and pregelatinised starch either from above or from the side or below. By choosing a suitable flow of starch seeds and the slurry of starch granules and pregelatinised starch, the seeds are coated, and the diameter is growing. Addition of the slurry of starch granules and pregelatinised starch is either continuous or it is repeated several times. Coating is continued until the particles have reached the desired diameter. When the particles reach the desired weight the particles will drop to the bottom and can be removed and classified.

Another technology for producing the agglomerated starch granules from the present invention is a Fluid Drum Granulator (available from Kaltenbach-Thüring, and described in Nitrogen vol. 196 3–6 (March–April 1992)). Such a granulator contains a horizontally-aligned cylindrical granulating drum which rotates around its axis. This type of granulator differs from the conventional granulator by having an internal fluidized bed. Product (starch seeds) flows down the inclined base of the bed and falls into the lower part of the drum. There it is sprayed with the slurry of starch granules and pregelatinised starch and the coated starch seed is lifted back to the fluidised bed, where the new layer solidifies. The same cycle is then repeated as many times as are necessary.

Other types of processes may be used. As long as it is a process for producing an agglomerated, substantially spherical starch particle characterized in that starch seeds are sprayed with a slurry of starch granules and pregelatinesed starch and the seeds are layered with the slurry, and the spraying and subsequent layering is repeated until the particles have reached a desired diameter. The process can be performed in batch or continuously, preferably it is a continuous process.

In order to obtain a reasonable agglomeration it is generally enough to use from about 1 to 20% (w/w) of the starch in pregelatinised form, preferably 2 to 10% of the starch is in pregelatinised form, more preferably from 4 to 8%.

Since only a minor amount of starch seeds is used initially, the aforementioned percentage is also the content of pregelatinised starch in the slurry while the residual amount of starch in the slurry is present as starch granules.

The agglomerated starch particles according to this invention are used in a series of applications and can be loaded with enzymes, pharmaceuticals, colorants, flavours, carotenoids, vitamins, and/or antifoams.

The agglomerated starch particles loaded with enzymes, pharmaceuticals, colorants, flavours, carotenoids, vitamins, and/or antifoams can be prepared by adding enzymes, pharmaceuticals, colorants, flavours, carotenoids, vitamins, and/or antifoams to the slurry of starch granules and pregelatinised starch or to the last layer when the particles are reaching their final diameter in the process.

Furthermore these loaded agglomerated starch particles can be obtained by using the agglomerated substantially spherical starch particles having their appropriate diameter and prepared according to the process of the current invention and cover or coat these particles with enzymes, pharmaceuticals, colorants, flavours, carotenoids, vitamins, and/or antifoams.

As indicated above the starch particles of the present invention are prepared with a desired diameter, that covers a broad range of possible diameter. Moreover, the diameter can be regulated to a good degree by changing the flow the slurry of starch granules and pregelatinised starch and the air or other gas flow, which keeps the fluid bed in motion and dries the product. In addition, through the use of a suitable classifier or by sieving, the particle size diameter can be further kept within a narrow range. Apart from the diameter issue the particles show some further advantages. When compared with starch powder the flowability is considerably improved. In addition, the particles do not dust, which decreases the explosion risk when large quantities are used. The specific surface area is high so that high amounts of products are absorbed. It is possible to incorporate the products to be included in the particles in the process at a desired stage so that the products can be in the particles or on the surface of the carrier. This process results in an increased flowability of the particles compared with starch powders or flours. As indicated above the use of starch mixtures is also possible.

When compared with mineral particles the starch particles show much lower abrasiveness. In addition starch can be incorporated in food or feed.

The agglomerated substantially spherical particles can be characterised by their hardness measured with a texture analyser (Stable Micro Systems TA-XT2). A cylindrical probe is applied onto the spherical particles and the compression force is measured.

EXAMPLES

Example 1

Preparation of Starch Particles with Specific Diameter 0.77 kg of pregelatinised starch (Cerestar C☆Gel Instant 12018) was dissolved in 25 kg water. 14.9 kg regular corn starch (Cerestar RG 03408) was added under gentle stirring. The slurry concentration was 38.5% c.b. 3 kg of seeds were added to a fluid bed for starting the process and heated to 45° C. The slurry was then sprayed over the powder and after a certain time the processed granules were discharged. The dryer was a fluid bed dyer type 28 (APV-DK Soborg, Denmark), with electrical heating and a perforated sheet area of 0.05 m2. The spraying was continuous and the particles were collected after different periods of time. The following granules were obtained.

| Sample No. | | 1a | 1b | 1c | 2a | 3a | 3b |
|---|---|---|---|---|---|---|---|
| Time | min | 60 | 120 | 180 | 240 | 270 | 315 |
| Granulation liq. Flow | kg/h | 5.65 | 5.65 | 5.65 | 5.88 | 8.14 | 8.14 |
| Inlet air T | ° C. | 110 | 115 | 110 | 110 | 112 | 112 |
| Powder layer T | ° C. | 45 | 45 | 46 | 46 | 37 | 37 |
| POWDER data | | | | | | | |
| Residual moisture | % | 8.4 | 9.3 | 8.8 | 8.8 | 13.1 | 13.4 |
| Bulk density (loose) | kg/l | 0.48 | 0.49 | 0.49 | 0.47 | 0.46 | 0.46 |
| Bulk density (packed) | kg/l | 0.57 | 0.55 | 0.56 | 0.54 | 0.52 | 0.52 |
| Mean particle size | μm | 350 | 400 | 450 | 560 | 630 | 690 |

The particle size depends on the time the spraying is continued.

Measurement of Hardness with Texture Analyser

The compressibility of the agglomerated spherical particles was measured by applying a texture analyser (Stable Micro Systems TA-XT2) in the mode of "force in compression" with a 25-mm cylinder probe using high resolution and 250 kg load cell.

Strips of 50 mm adhesive tape were cut at a length of approx. 150 mm and the particles were gently poured over the tape and an even covering of the tape surface was ensured. The tape was placed on the base plate and the compression test was commenced by moving the cylinder probe with a speed of 0.1 mm/s and a distance of 2.5 mm form the base plate down to the particles. On contact with the particles (fraction of 500–710 μm), a rise in force was observed as the probe continued to compress the sample. This rise in force continued until the probe has moved 2.1 mm downwards and the maximum force was taken as the hardness of the product.

The hardness of some of the products was determined:

1b: 8.2 kg, 1c: 10.4 kg and 2a: 15 kg.

The hardness increased in time also. The products were hard enough for most of the normal applications.

The process when repeated with an enzyme likewise gave a suitable product.

Example 2

Influence of the Amount of Pregelatinised Starch in the Starting Product

The base product was either starch granules alone (sample 2) or a mixture of starch granules and pregelatinised starch (sample 1).

A slurry containing starch granules and pregelatinised starch was sprayed over the base product in a lab scale V-blender (NIRO).

The results were as follows.

| Sample No. | 1 | 2 |
|---|---|---|
| Base product | 96% 03408 | 100% 03408 |
| | 4% 12018 | |
| Slurry | 36.1% 03408 | 36.1% 03408 |
| | 1.9% 12018 | 1.9% 12018 |
| Moisture of the mixture | 43.2% | 42.9% |
| Pregelatinised starch amount | 4.7 % | 0–2.1% |
| Inlet drying T | 90° C. | 107° C. |
| Drying time | 38 min | 38 min |
| POWDER data | | |
| Residual moisture | 10.3% | 13% |
| Particle size | | |
| <355 μm | 26% | 42% |
| 355–710 μm | 31% | 40% |
| >710 μm | 43% | 18% |

From the results it can be seen that the particles are bigger when more initial pregelatinised starch is added.

In addition, the hardness was measured according to the previously described method. The hardness of Sample 1 was 17.5 kg and that of Sample 2 was 14.1 kg.

What is claimed is:

1. An agglomerated, substantially spherical particle characterised in that the particle is comprising 100% starch (w/w) and said particle consists of successive layers comprising starch granules and pregelatinised starch and said particle has a diameter of from 50 μm to 3 mm.

2. A particle according to claim 1, wherein the particle has a diameter of from 100 μm to 2 mm.

3. A particle according to claim 1 characterized in that the starch is selected from the group consisting of rice, wheat, corn, potato, sago, bean and tapioca starch and mixtures thereof.

4. A particle according to claim 2, wherein the particle has a diameter of from 300 μm to 800 μm.

5. A particle according to claim 1, wherein the particle has a hardness value of between 8.2 and 17.5 kg as measured in a force in compression mode of a texture analyzer.

6. An agglomerated, substantially spherical particle having a diameter of 50 μm to 3 mm which comprises 100% starch (w/w) and one or more members selected from the group consisting of an enzyme, a pharmaceutical, a colorant, a flavour, a carotenoid, a vitamin and an antifoam, wherein said particle consists of successive layers formed from starch granules and pregelatinized starch, and wherein at least one of said successive layers contains at least one of said members.

7. A particle according to claim 5, wherein the particle has a diameter of from 100 μm to 2 mm.

8. A particle according to claim 6, wherein said particle has a diameter of from 300 μm to 800 mm.

9. A particle according to claim 6, wherein the outer most layer of said particle contains at least one member selected from the group consisting of an enzyme, a pharmaceutical, a colorant, a flavour, a carotenoid, a vitamin and an antifoam.

10. A process for producing an agglomerated, substantially spherical starch particle which comprises:

spraying starch seeds with a slurry of starch granules and pregelatinized starch, said slurry having a concentration of at least 20% w/w on a dry surface bases, and layering said seeds with said slurry; and repeating said spraying and subsequent layering until particles are obtained which have a final diameter of from 50 μm to 3 mm.

11. A process according to claim 10, wherein said process at least one member selected from the group consisting of an enzyme, a pharmaceutical, a colorant, a flavour, a carotenoid, a vitamin and antifoam is added to the slurry of starch granules and pregelatinized starch which is being used to form at least one said layer.

12. A process according to claim 11, wherein at least one member is added to the slurry being used in the formation of a last layer on said particles when said particles are reaching their final diameter.

13. A process according to claim 10, wherein said spraying is conducted at an air temperature of 110° C.

14. A process according to claim 10, wherein the particles obtained have a hardness of 17.5 kg, 26% of the particles have a diameter less than 355 μm, 31% of the particles have a diameter between 355 and 710 μm, and 43% of said particles have a diameter greater than 710 μm.

15. A process according to claim 10, wherein said process further comprises covering the agglomerated substantially spherical starch particles with at least one member selected from the group consisting of an enzyme, a pharnaceutical, a colorant, a flavour, a carotenoid, a vitamin and an antifoam.

16. A process according to any one of claims 10–15, wherein said process is performed in a fluid bed reactor, a fluid drum granulator or a blender.

\* \* \* \* \*